(12) United States Patent
Dubey et al.

(10) Patent No.: US 8,124,783 B2
(45) Date of Patent: Feb. 28, 2012

(54) PROCESS FOR PRODUCING 1-BENZYL-4-[5,6-DIMETHOXY-1-INDANON-2-YL)METHYL] PIPERIDINE OR ITS SALT THEREOF VIA NOVEL INTERMEDIATE

(75) Inventors: Shailendra Kumar Dubey, Noida (IN); Amit Kumar Sharma, Noida (IN); Beena S. Rani, Noida (IN); Soumendu Paul, Noida (IN); Rajesh Kumar Thaper, Noida (IN); Dubey Sushil Kumar, Noida (IN); Jag Mohan Khanna, Noida (IN)

(73) Assignee: Jubilant Organosys Limited, Noida, Uttar Pradesh (IN)

( * ) Notice: Subject to any disclaimer, the term of this patent is extended or adjusted under 35 U.S.C. 154(b) by 1120 days.

(21) Appl. No.: 11/813,093

(22) PCT Filed: Dec. 30, 2004

(86) PCT No.: PCT/IN2004/000433
§ 371 (c)(1),
(2), (4) Date: Dec. 3, 2007

(87) PCT Pub. No.: WO2006/070396
PCT Pub. Date: Jul. 6, 2006

(65) Prior Publication Data
US 2009/0137812 A1    May 28, 2009

(51) Int. Cl.
*C07D 211/82* (2006.01)
*C07D 211/70* (2006.01)
(52) U.S. Cl. ......... 546/342; 546/205; 546/206; 546/238

(58) Field of Classification Search .............. 546/205, 546/206, 238, 342
See application file for complete search history.

(56) References Cited

U.S. PATENT DOCUMENTS

| | | | |
|---|---|---|---|
| 4,895,841 A | 1/1990 | Sugimoto et al. | |
| 5,606,064 A | 2/1997 | Lensky | |
| 6,252,081 B1 | 6/2001 | Iimura | |
| 6,649,765 B1 | 11/2003 | Vidyadhar et al. | |
| 6,706,741 B2 | 3/2004 | Iimura et al. | |
| 7,148,354 B2 * | 12/2006 | Reddy et al. | 546/206 |
| 2004/0143121 A1 | 7/2004 | Reddy et al. | |
| 2004/0158070 A1 | 8/2004 | Radhakrishnan et al. | |

FOREIGN PATENT DOCUMENTS

| WO | WO9805327 | * 2/1998 |
|---|---|---|
| WO | WO 2004/082685 | 9/2004 |

OTHER PUBLICATIONS

Rehse et al. "2-methylene- . . . " Verlag Chemie GmbH, p. 54-58 (1984).*
Zacharie et al "A mild procedure . . . " J. Org. Chem. 66, 5264-5265 (2001).*
Kim et al. "C-8 substituted . . . " J. Med. Chem. 46, 2216-2226 (2003).*
Database CAPLUS on STN (Columbus, OH, USA) No. 100:79488 '2-methylene-1,3-indandionese:azaaromatic anticoagulants without enolizabile functions' Abstract, Rehse et al. (1984).

* cited by examiner

*Primary Examiner* — Celia Chang
(74) *Attorney, Agent, or Firm* — Workman Nydegger

(57) ABSTRACT

Disclosed herein the process for producing 1-benzyl-4-[(5,6-dimethoxy-1-indanon-2yl)methyl]piperidine or its salt thereof employing novel intermediates.

26 Claims, No Drawings

PROCESS FOR PRODUCING 1-BENZYL-4-[5,6-DIMETHOXY-1-INDANON-2-YL)METHYL] PIPERIDINE OR ITS SALT THEREOF VIA NOVEL INTERMEDIATE

FIELD OF THE INVENTION

This invention in general relates to a process for producing 1-benzyl-4-[(5,6-dimethoxy-1-indanon-2-yl)methyl]piperidine or its salt thereof. More particularly, the present invention provides a process for producing pure 1-benzyl-4-[(5,6-dimethoxy-1-indanon-2-yl)methyl]piperidine or its salt thereof employing novel intermediates.

BACKGROUND OF THE INVENTION

1-Benzyl-4-[(5,6-dimethoxy-1-indanon-2-yl)methyl]piperidine (Donepezil) of formula 1, is a new drug used in the treatment of mild to moderate cases of SDAT (Senile Dementia of Alzheimers Type).

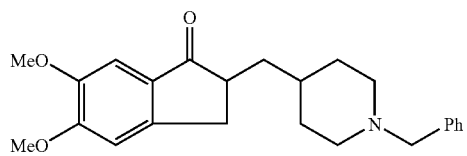
(1)

There are many processes as disclosed in the prior arts for producing donepezil of formula 1. U.S. Pat. No. 4,895,841 wherein substituted 1-indanone-2-phosphonate prepared from 2-bromo-5,6-dimethoxyindanone and triethyl phosphite, is treated with 1-benzylpiperidine-4-carboxaldehyde in the presence of a strong base, such as lithium diisopropylamide (LDA), followed by catalytic reduction using palladium on carbon in tetrahydrofuran (40 volumes) to yield donepezil with an overall yield of 50.8%. This process however suffers with few limitations i.e. it employs triphenylphosphonium methoxymethyl chloride, which is expensive and toxic and the overall yield of this process is quite low. (scheme 1).

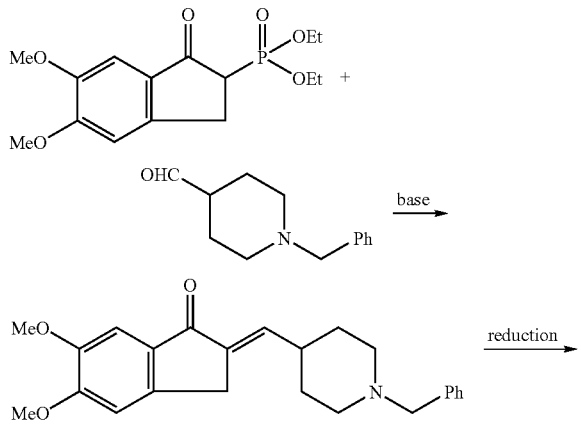

Scheme 1

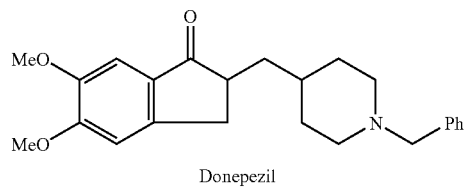

Donepezil

U.S. Pat. No. 5,606,064 describes another route to prepare donepezil via the reduction of 1-benzyl-4-[(5,6-dimethoxy-1-indanon-2-ylidene)methyl]pyridinium salt in presence of platinum dioxide as catalyst and methanol as solvent with a yield of 58.5% (scheme 2). However, the reduction of an olefinic bond and a pyridinium ring in presence of a benzyl group, as described in the process is difficult to achieve and leads to unwanted side products mainly debenzylated product and the reaction time for completion is also too long which is 24 hrs.

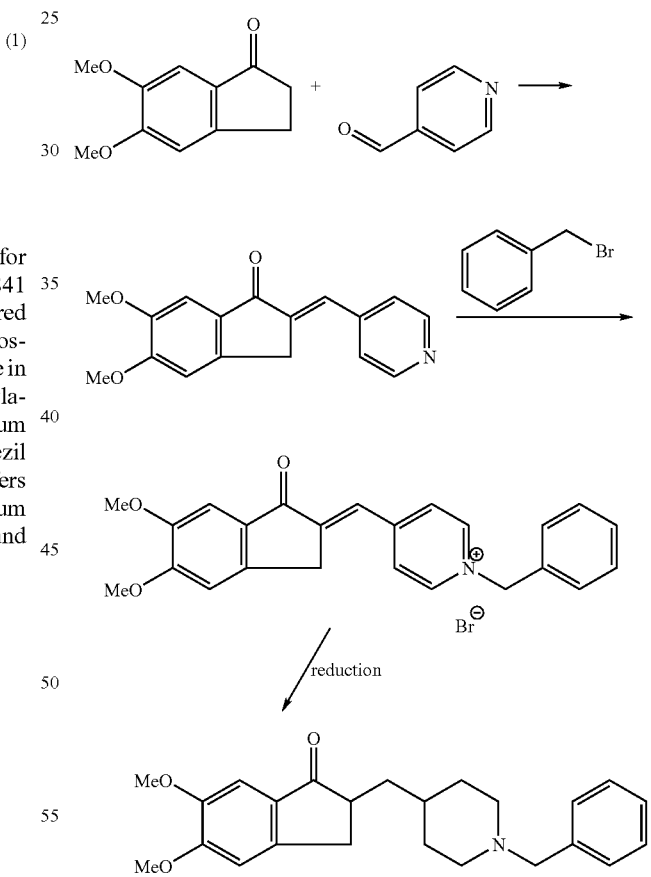

Scheme 2

U.S. Pat. No. 6,252,081 discloses a process, which involves the selective reduction of pyridinium ring of 1-benzyl-4-[(5,6-dimethoxy-1-indanon-2-yl)methyl]pyridinium salt using platinum oxide as catalyst and methanol (15 volumes) as a solvent. This process also leads to the formation of impurities, which are difficult to separate and affects the overall reaction yield along with the purity of the compound (Scheme 3).

Scheme 3

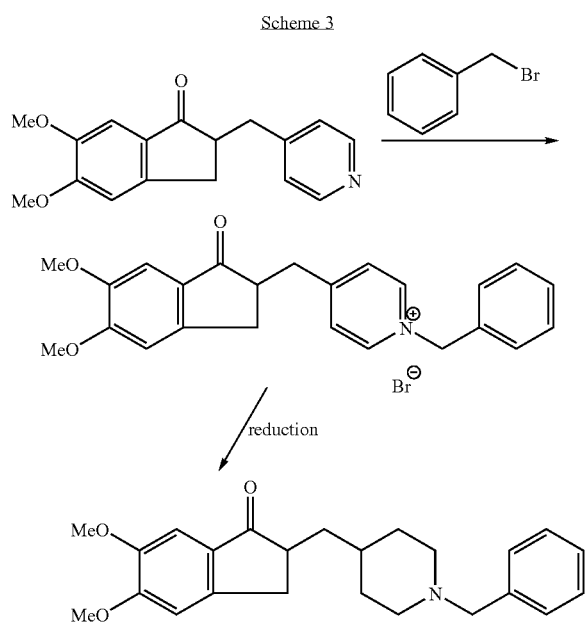

U.S. Pat. No. 6,649,765 and US Patent Application No. 20040158070 describe the synthesis of donepezil by the reduction of 4-[(5,6-dimethoxy-1-indanon-2-ylidene)methyl]pyridine using noble metal oxide or non-oxide noble metal catalyst in a mixture of solvents such as acetic acid and methanol (30-40 volumes) at 25-50 psi gauge followed by benzylation (Scheme 4).

Scheme 4

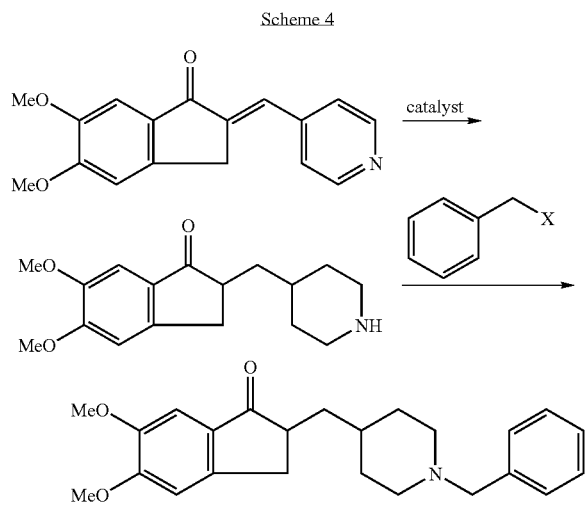

US Patent Application No. 20040143121 discloses the process for the preparation of donepezil which involves the reduction of compound 4-[(5,6-dimethoxy-1-indanon-2-ylidene)methyl]pyridine using platinum dioxide or Pd/C as catalyst, and in a mixture of solvents such as acetic acid and methanol (15-20 volumes), whereas WO 2004082685 describes the preparation of donepezil which comprises the two step reduction starting from 4-[(5,6-dimethoxy-1-indanon-2-ylidene)methyl]pyridine via the preparation of intermediate 4-[(5,6-dimethoxy-1-indanon-2-yl)methyl]pyridine using mixture of methanol and methylene chloride as a solvent (20-25 volumes).

The processes disclosed in the prior art have several limitations like multiple chemical steps, overall low yields, side product formation, use of expensive or hazardous reagents. Furthermore, the most common drawback is the use of very large, usually 15-40 volume of solvent as well as large amount of noble metal catalyst usually 10% in the hydrogenation step. The use of such large volume of solvent in the hydrogenation step is a major safety risk. Moreover, it creates not only handling problem but subsequently large volume of solvents has to be distilled off to isolate the hydrogenated product. Thus the productivity of the hydrogenation reactor is severely curtailed and it becomes a bottleneck in the large-scale production of donepezil. The reason for the use of large volume of solvent could be the poor solubility of the pre-hydrogenation intermediates. Therefore, there is a need to develop novel pre-hydrogenation intermediates, which would be easily soluble in the solvents commonly used in the hydrogenation step to make the large-scale production of donepezil safe and yet economically feasible.

Present invention bridges this gap and discloses a novel process, which eliminates the excessive use of solvent in the hydrogenation step and is suitable for industrial scale up.

SUMMARY OF THE INVENTION

It is, therefore, a principal aspect of the present invention to provide a novel way for producing 1-benzyl-4-[(5,6-dimethoxy-1-indanon-2-yl)methyl]piperidine of formula (1) or its salt thereof over limitations in the prior art. These and other objects are attained in accordance with the present invention wherein there is provided several embodiments of the process for producing 1-benzyl-4-[(5,6-dimethoxy-1-indanon-2-yl)methyl]piperidine or its salt thereof employing novel intermediates.

Accordance with one preferred embodiment of the present invention, there is provided a novel process for producing 1-benzyl-4-[(5,6-dimethoxy-1-indanon-2yl)methyl]piperidine or its salt thereof employing an intermediate 4-[(5,6-dimethoxy-1-indanon-2-yl)methyl]piperidine of formula (2) or its salt thereof in a way to improve the yield and purity and obviates the formation of byproduct.

Accordance with another preferred embodiment of the present invention, there is provided a novel process for producing 1-benzyl-4-[(5,6-dimethoxy-1-indanon-2-yl)methyl]piperidine or its salt thereof employing a novel intermediate 4-[(5,6-dimethoxy-1-indanon-2-ylidene)methyl]pyridine N-oxide of formula (3).

Accordance with yet another preferred embodiment of the present invention, there is provided a novel process for producing 1-benzyl-4-[(5,6-dimethoxy-1-indanon-2-yl)methyl]piperidine or its salt thereof employing a novel intermediate 4-[(5,6-dimethoxy-1-indanon-2-yl)methyl]pyridine N-oxide of formula (6).

Accordance with yet another preferred embodiment of the present invention, there is provided a process for preparation of an intermediate 4-[(5,6-dimethoxy-1-indanon-2-yl)methyl]piperidine of formula (2) or its salt thereof used in the production of 1-benzyl-4-[(5,6-dimethoxy-1-indanon-2-yl)methyl]piperidine of formula (1) or its salt thereof. The process comprises oxidation of 4-[(5,6-dimethoxy-1-indanon-2-ylidene)methyl]pyridine of formula (4) to get its N-oxide derivative (3), which on reduction gives 4-[(5,6-dimethoxy-1-indanon-2-yl)methyl]piperidine of formula (2) or its salt thereof.

Accordance with yet another preferred embodiment of the present invention, there is provided a process for preparation of an intermediate 4-[(5,6-dimethoxy-1-indanon-2-yl)methyl]piperidine of formula (2) or its salt thereof by selectively reducing the double bond of 4-[(5,6-dimethoxy-1-indanon-2-ylidene)methyl]pyridine of formula (4) and then oxidizing the resultant reduced intermediate of formula (5) to get its N-oxide derivative (6), which on further reduction gives 4-[(5,6-dimethoxy-1-indanon-2-yl)methyl]piperidine of formula (2) or its salt thereof.

DETAILED DESCRIPTION OF THE INVENTION

The disclosed embodiment of the present invention deals with a process for producing 1-benzyl-4-[(5,6-dimethoxy-1-indanon-2-yl)methyl]piperidine of formula (1) or its salt thereof by using novel intermediates.

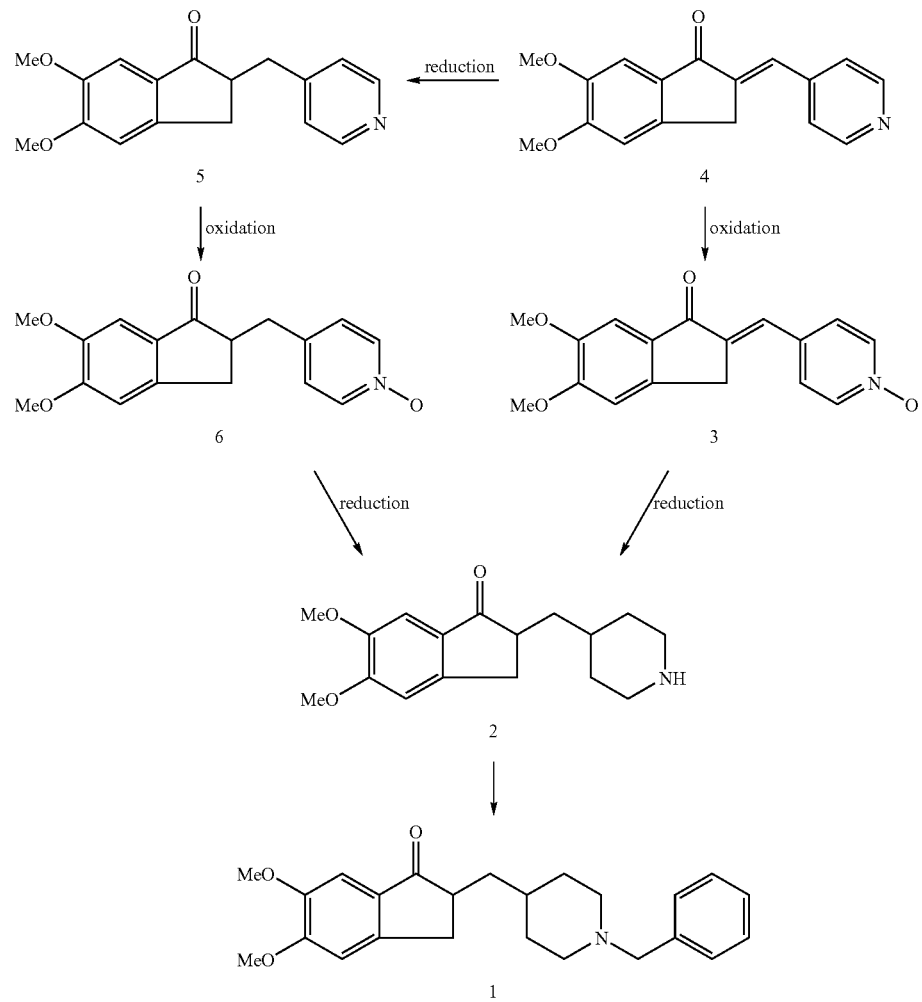

Scheme 5

Accordance with yet another preferred embodiment of the present invention, there is provided a process for producing 1-benzyl-4-[(5,6-dimethoxy-1-indanon-2-yl)methyl]piperidine of formula (1) or its salt thereof, wherein the intermediate 4-[(5,6-dimethoxy-1-indanon-2-yl)methyl]piperidine of formula (2) or its salt thereof is further treated with benzylating agent to get final product 1-benzyl-4-[(5,6-dimethoxy-1-indanon-2-yl)methyl]piperidine of formula (1) or its salt thereof.

Accordance with still another preferred embodiment of the present invention, there is provided a novel pre-hydrogenation intermediate 4-[(5,6-dimethoxy-1-indanon-2-ylidene)methyl]pyridine N-oxide of formula (3).

Accordance with still another preferred embodiment of the present invention, there is provided a novel pre-hydrogenation intermediate 4-[(5,6-dimethoxy-1-indanon-2-yl)methyl]pyridine N-oxide of formula (6).

The present invention in its aspect is a new, improved, economical and industrially feasible method for preparing donepezil (1). The donepezil (1) is prepared from 4-[(5,6-dimethoxy-1-indanon-2-yl)methyl]piperidine or its salt thereof (2), which is the key intermediate, whose preparation is outlined in scheme 5 and comprises:

(a) oxidizing 4-[(5,6-dimethoxy-1-indanon-2-ylidene)methyl]pyridine (4) using oxidizing agent in solvent to yield its N-oxide derivative (3);
(b) reducing N-oxide derivative (3) in presence of hydrogenating catalyst in solvent to yield 4-[(5,6-dimethoxy-1-indanon-2-yl)methyl]piperidine or salt thereof (2).

Alternatively 4-[(5,6-dimethoxy-1-indanon-2-yl)methyl]piperidine or salt thereof (2) is also prepared by:
(a) reducing selectively the double bond of 4-[(5,6-dimethoxy-1-indanon-2-ylidene)methyl]pyridine (4) in presence of catalyst in solvent to yield the 4-[(5,6-dimethoxy-1-indanon-2-yl)methyl]pyridine (5);

(b) treating 4-[(5,6-dimethoxy-1-indanon-2-yl)methyl]pyridine (5) with an oxidizing agent in solvent to get its N-oxide derivative (6);

(c) reducing N-oxide derivative (6) in presence of hydrogenating catalyst in solvent to yield 4-[(5,6-dimethoxy-1-indanon-2-yl)methyl]piperidine (2) or its salt thereof.

The above mentioned processes further comprises the N-benzylation of 4-[(5,6-dimethoxy-1-indanon-2-yl)methyl]piperidine or its salt thereof (2) in presence of a base optionally in presence of phase transfer catalyst, followed by preparation of pharmaceutical acceptable salt of 1-benzyl-4-[(5,6-dimethoxy-1-indanon-2-yl)methyl]piperidine (1).

4-[(5,6-dimethoxy-1-indanon-2-ylidene)methyl]pyridine (4) is oxidized with oxidizing agent in solvent to afford its N-oxide derivative (3).

The oxidizing agent used herein is selected from the group consisting of but not limited to peracids such as peracetic acid, caro's acid, m-chloroperoxybenzoic acid, oxaziridines, oxiranes such as dimethyldioxirane (DMD), peroxides such as hydrogen peroxide-acetic acid, bis(trimethylsilyl)peroxide (BTSP) or metalloorganic oxidizing agents such as hydrogen peroxide-manganese tetrakis(2,6-dichlorophenyl)porphyrin, hydrogen peroxide-methyltrioxorhenium (MTO), preferably peracetic acid or m-chloroperoxybenzoic acid. The reaction is carried out in solvent selected from the group consisting of lower alcohol having 1 to 4 carbon atoms, chlorinated hydrocarbons such as methylene chloride, acetonitrile, dimethylformamide and water or mixture thereof. The reaction is carried out at a temperature from 0° C. to 85° C.

N-oxide derivative (3) is highly soluble than its starting material due to which solvent needed for the hydrogenation reaction is substantially low (5-10 volumes) as compared to the quantity reported (15-40 volumes) in the prior art so far. Low volume of the solvent in the hydrogenation reaction is much easy to handle on manufacturing scale and furthermore, time needed to recover the solvent after hydrogenation is substantially reduced, thereby increasing the productivity and reducing the safety risk. Because of the low volume, quantity of catalyst required for hydrogenation is also reduced to half (5% w/w Pd/C as compared to prior art i.e. 10% w/w). Moreover, N-oxide derivative is very easy to prepare in quantitative yields.

Compound of formula (3) is then reduced to get the 4-[(5,6-dimethoxy-1-indanon-2-yl)methyl]piperidine or salt thereof (2). In general the reduction may be achieved by hydrogenation in the presence of catalyst. The catalyst used for the reduction are the customary hydrogenation catalysts known in the organic chemistry for example but not limited to noble metals or their derivatives such as platinum, palladium, rhodium, ruthenium and the like, optionally in presence of an acid such as hydrochloric acid, acetic acid, perchloric acid or formic acid. The reaction is carried out in solvent or mixture thereof. The solvent used is selected from the group consisting of but not limited to ethers such as dibutyl ether, methyl tert-butyl ether, dioxane and tetrahydrofuran, lower alcohols such as methanol, ethanol, propanol, isopropanol and butanol, chlorinated hydrocarbons such as methylene chloride, esters such as ethyl acetate and isopropyl acetate, polar aprotic solvents such as dimethylformamide, dimethyl sulfoxide, N-methylpyrrolidone and water or mixture thereof. The hydrogenation may be carried out at normal pressure or at elevated pressure depending on the choice of catalyst. It may be carried out at a hydrogen pressure in the range from 30 psi to 200 psi. In particular, it may be carried out at a hydrogen pressure in the range from 80-100 psi. The hydrogenation may be carried out at a temperature from about 30° C. to 110° C., for example from about 50° C. to about 80° C.

Alternatively preparation of 4-[(5,6-dimethoxy-1-indanon-2-yl)methyl]piperidine or salt thereof (2), comprises the selective reduction of the double bond of compound of formula (4) to get 4-[(5,6-dimethoxy-1-indanon-2-yl)methyl]pyridine (5).

In general, the reduction of the compound of formula (4) to 4-[(5,6-dimethoxy-1-indanon-2-yl)methyl]pyridine (5) may be achieved by selective hydrogenation in the presence of catalyst or by other conventional procedures for carbon-carbon double bond reduction, which do not reduce the pyridine ring of the compound of formula (4). The catalyst used for the selective hydrogenation is the customary hydrogenation catalyst used under milder conditions known in the organic chemistry. Example of catalyst used for hydrogenation is selected from the group consisting of but not limited to zinc-acetic acid, Fe—HCl, Raney Ni, noble metals or their derivatives such as platinum, palladium, rhodium, ruthenium and the like. The reaction with noble metals or their derivatives can be carried out optionally in presence of catalytic amount of an acid such as perchloric acid. The solvent used in the reaction is selected from the group consisting of but not limited to ethers such as dibutyl ether, methyl tert-butyl ether, dioxane and tetrahydrofuran, lower alcohols such as methanol, ethanol, propanol, isopropanol and butanol, chlorinated hydrocarbons such as methylene chloride, esters such as ethyl acetate and isopropyl acetate, polar aprotic solvents such as dimethylformamide, dimethyl sulfoxide, N-methylpyrrolidone and water or mixture thereof. The hydrogenation may be carried out at normal pressure or at elevated pressure depending on the choice of catalyst. It may be carried out at a hydrogen pressure in the range from 20 psi to 60 psi. In particular, it may be carried out at a hydrogen pressure in the range from 20-30 psi. The hydrogenation may be carried out at a temperature from about 10° C. to 40° C.

4-[(5,6-Dimethoxy-1-indanon-2-yl)methyl]pyridine (5) is then oxidized with an oxidizing agent in solvent to afford a compound of formula (6). The oxidizing agent used is selected from the group consisting of but not limited to peracids such as peracetic acid, caro's acid, m-chloroperoxybenzoic acid, oxaziridines, oxiranes such as dimethyldioxirane (DMD), peroxides such as hydrogen peroxide-acetic acid, bis(trimethylsilyl)peroxide (BTSP) or metalloorganic agents such as hydrogen peroxide-manganese tetrakis(2,6-dichlorophenyl)porphyrin, hydrogen peroxide-methyltrioxorhenium (MTO), preferably peracetic acid or w-chloroperoxybenzoic acid. The reaction is carried out in solvent selected from the group consisting of but not limited to lower alcohol having 1 to 4 carbon atoms, chlorinated hydrocarbons such as methylene chloride, acetonitrile, dimethylformamide and water or mixture thereof. The reaction is carried out at a temperature from 0° C. to 85° C.

The compound of formula (6) is then reduced to get 4-[(5,6-dimethoxy-1-indanon-2-yl)methyl]piperidine or salt thereof (2). In general the reduction may be achieved by hydrogenation in the presence of catalyst. The catalyst used for the reduction are the customary hydrogenation catalysts known in the organic chemistry for example but not limited to noble metals or their derivatives such as platinum, palladium, rhodium, ruthenium and the like, optionally in presence of an acid such as hydrochloric acid, acetic acid, perchloric acid or formic acid. The reaction is carried out in solvent or mixture thereof. The solvent used is selected from the group consisting of but not limited to ethers such as dibutyl ether, methyl tert-butyl ether, dioxane and tetrahydrofuran, lower alcohols such as methanol, ethanol, propanol, isopropanol and butanol, chlorinated hydrocarbons such as methylene chloride, esters such as ethyl acetate and isopropyl acetate, polar aprotic solvents such as dimethylformamide, dimethyl sulfoxide, N-methylpyrrolidone and water or mixture thereof. The hydrogenation may be carried out at normal pressure or at elevated pressure depending on the choice of catalyst. It may be carried out at a hydrogen pressure in the range from 30 psi to 200 psi. In particular, it may be carried out at a hydrogen pressure in the range from 80-100 psi. The hydrogenation may be carried out at a temperature from about 30° C. to 110° C., for example from about 50° C. to about 80° C.

Compound of formula (2) prepared from any of the above-mentioned processes is then transformed into donepezil (1) by reacting with benzylating agent, in presence of base in solvent, optionally in the presence of phase transfer catalyst. The base used is from the group consisting of inorganic or organic bases. The inorganic base is selected from the group consisting of but not limited to carbonates or bicarbonates of alkali metal like potassium, sodium, lithium and the like preferably potassium carbonate and the organic base is selected from the group consisting of but not limited to triethyl amine, pyridine, N-methyl morpholine, N,N-dimethyl benzyl amine, picoline or lutidine. The benzylating agent used is from the group consisting of but not limited to benzyl bromide, benzyl chloride, benzyl iodide, benzyl mesylate or benzyl tosylate.

The phase transfer catalyst used is selected from the group consisting of but not limited to ammonium based phase transfer reagent, phosphonium based phase transfer reagent, crown ethers or polyethylene glycols for example tetrabutylammonium iodide, tetrabutylammonium bromide, tetrabutylammonium hydrogen sulfate, benzyl triethylammonium chloride, benzyl tributylammonium chloride, tetramethylammonium chloride, tetrabutylphosphonium chloride, dibenzo-18-crown-6, PEG-200 or PEG-400, preferably tetrabutylammonium iodide (TBAI) or PEG-200. The solvent used is selected from the group consisting of ethers such as diethyl ether, dibutyl ether, methyl tert-butyl ether, dioxane and tetrahydrofuran; chlorinated hydrocarbons such as methylene chloride; esters such as ethyl acetate and isopropyl acetate; ketones such as acetone and methyl isobutyl ketone (MIBK); alcohols such as methanol, ethanol, propanol and isopropanol; acetonitrile; dimethylformamide; dimethyl sulfoxide; 1,2-dimethoxyethane; N-methylpyrrolidone; sulpholane; water or mixture thereof. The benzylation reaction is carried out at a temperature range from about 0° C. to 110° C., for example from about 0° C. to about 80° C. In particular, it may be carried out at a temperature from about 25° C. to about 60° C. The primary use of phase transfer catalyst in benzylation reaction is to reduce the reaction time for completion. It also reduces the side product formation during the reaction, which credited to the enhancement in the yield as well purity of 1-benzyl-4-[(5,6-dimethoxy-1-indanon-2-yl)methyl]piperidine (1).

1-Benzyl-4-[(5,6-dimethoxy-1-indanon-2-yl)methyl]piperidine (1) can optionally be prepared directly from the reaction mixture obtained from the hydrogenation reaction of compound of formula 3 or 6 without isolating the intermediate compound of formula 2. For this, reaction mixture is first filtered to remove the hydrogenating catalyst and then filtrate is further treated with base and benzylating agent in solvent to get 1-benzyl-4-[(5,6-dimethoxy-1-indanon-2-yl)methyl]piperidine (1).

1-Benzyl-4-[(5,6-dimethoxy-1-indanon-2-yl)methyl]piperidine (1) is then converted to its pharmaceutically acceptable salt as donepezil hydrochloride by treating with hydrochloric acid in presence of solvent such as alcohol, aliphatic ether or mixture thereof. Most preferably the solvent is selected from methanol, ethanol, diethyl ether or diisopropyl ether and the like.

In conclusion, this is a novel, economical and a high yielding process for the industrial production of donepezil using cheaply available raw materials.

The following non-limiting examples illustrate specific embodiments of the present invention. They are, however, not intended to be limiting the scope of present invention in any way.

Example 1

Preparation of 4-[(5,6-dimethoxy-1-indanon-2-ylidene)methyl]pyridine (4)

A mixture of 5,6-dimethoxy-indan-1-one (10 g), pyridine-4-carboxaldehyde (7.8 g), p-toluenesulphonic acid (13.8 g) in toluene (120 ml) was refluxed azeotropically for 6 hours. The reaction mixture was cooled to room temperature and filtered. The wet solid so obtained was stirred with 10% aqueous sodium carbonate solution. The solid was filtered, washed with acetone and then dried to get the title compound (13.2 g).

Example 2

Preparation of 4-[(5,6-dimethoxy-1-indanon-2-ylidene) methyl]pyridine N-oxide (3)

4-[(5,6-Dimethoxy-1-indanon-2-ylidene)methyl]pyridine (2.5 g) was dissolved in methylene chloride (60 ml) and chilled. m-Chloroperbenzoic acid (2.0 g) was added to reaction mixture and then stirred for 4 hours. Solid obtained was filtered. The wet solid so obtained was stirred with 10% sodium bicarbonate solution. The solid was filtered, washed with acetone and then dried to get the title compound (2.5 g).

IR (KBr, cm$^{-1}$): 3434, 2914, 1685, 1628, 1606, 1503, 1310, 1259, 1231, 1182, 1168, 1128, 1086, 1000, 819.

$^1$H-NMR (400 MHz, CDCl$_3$, δ ppm): 3.95 (s, 2H, C$_3$—H), 3.96 (s, 3H, C$_{11}$—H), 4.01 (s, 3H, C$_{10}$—H), 6.98 (s, 1H, C$_4$—H), 7.34 (s, 1H, C$_7$—H), 7.42 (m, 1H, C$_{12}$—H), 7.50 (m, 2H, C$_{14}$—H and C$_{15}$—H), 8.24 (m, 2H, C$_{16}$—H and C$_{17}$—H).

$^{13}$C-NMR (400 MHz, CDCl$_3$, δ ppm): 31.97, 56.23, 56.34, 105.17, 106.9, 126.67, 126.91, 130.67, 138.78, 139.45, 144.36, 150.03, 156.07, and 192.01.

MS: 298 (M+1)$^+$.

Example 3

Preparation of Hydrochloride Salt of 4-[(5,6-dimethoxy-1-indanon-2-yl)methyl]piperidine (2)

4-[(5,6-Dimethoxy-1-indanon-2-ylidene)methyl]pyridine N-oxide (10 g) in methanol (50 ml) and methylene chloride (50 ml) was hydrogenated in presence of concentrated hydrochloric acid (1.18 g) and palladium on activated carbon (0.5 g). The reaction mixture was filtered, filtrate was concentrated and residue so obtained was crystallized from solvent to get the title compound (9.5 g).

Example 4

Preparation of 4-[(5,6-dimethoxy-1-indanon-2-yl)methyl]pyridine (5)

4-[(5,6-Dimethoxy-1-indanon-2-ylidene)methyl]pyridine (50 g) in methanol and dichloromethane (1:1) was hydrogenated in presence of palladium on carbon (5 g) and a catalytic quantity of perchloric acid at 0.5 kg pressure and room temperature. The solvents were evaporated under vacuum and the residue was taken in ethyl acetate (500 ml), washed with water (50 ml), brine (50 ml), dried over anhydrous sodium sulphate and evaporated in vacuum to yield the product. Yield: 49 g.

Example 5

Preparation of 4-[(5,6-dimethoxy-1-indanon-2-yl) methyl]pyridine N-oxide (6)

4-[(5,6-Dimethoxy-1-indanon-2-yl)methyl]pyridine (1.2 g) was dissolved in methylene chloride (18 ml) and chilled. m-Chloroperbenzoic acid (0.9 g) was added to reaction mixture and then stirred for 4 hours. Reaction mass was stirred with 10% aqueous solution of sodium bicarbonate. The organic layer was separated and washed with 50 ml water. Organic layer was distilled off, title compound is obtained (1.2 g).

IR (KBr, cm$^{-1}$): 3574, 3369, 3527, 3101, 2930, 1680, 1603, 1589, 1502, 1481, 1437, 1422, 1308, 1266, 1228, 1181, 1124, 1048, 1010, 796.

$^1$H-NMR (400 MHz, CDCl$_3$, δ ppm): 3.02 (m, 1H, C$_2$—H), 2.68, 3.07 (dd, 4H, C$_3$—H and C$_{12}$—H), 3.79 (s, 3H, C$_{11}$—H), 3.84 (s, 3H, C$_{10}$—H), 7.05 (s, 1H, C$_4$—H), 7.07 (s, 1H, C$_7$—H), 7.34 (m, 2H, C$_{14}$—H and C$_{15}$—H), 8.13 (m, 2H, C$_{16}$—H and C$_{17}$—H).

$^{13}$C-NMR (400 MHz, CDCl$_3$, δ ppm): 31.65, 34.97, 47.71, 56.12, 56.45, 104.43, 108.68, 127.45, 129.29, 138.56, 138.74, 149.20, 149.70, 155.94 and 205.35.

MS: 300 (M+1)$^+$, 322 (M$^+$+23).

Example 6

Preparation of Hydrochloride Salt of 4-[(5,6-dimethoxy-1-indanon-2-yl)methyl]piperidine (2)

4-[(5,6-Dimethoxy-1-indanon-2-yl)methyl]pyridine N-oxide (10 g) in methanol (100 ml) was hydrogenated in presence of conc. hydrochloric acid (1.18 g) and palladium on activated carbon (1 g). The reaction mixture was filtered, filtrate was concentrated and residue so obtained was crystallized from acetone to get the title compound (9.5 g).

Example 7

Preparation of 1-benzyl-4-[(5,6-dimethoxy-1-indanon-2-yl)methyl]piperidine (1)

4-[(5,6-Dimethoxy-1-indanon-2-yl)methyl]piperidine (4 g) was taken in acetone (60 ml). To which benzyl chloride (1.92 g), potassium carbonate (2.28 g) and a catalytic quantity of tetrabutylammonium iodide (TBAI) were added. The reaction mixture was heated at 60° C. and reaction was monitored on TLC. Solvent was removed by distillation after reaction completion and the residue was taken in water and extracted with ethyl acetate (100 ml). The organic extract was acidified with conc. HCl. The solvent was evaporated under vacuum to yield the salt as a residue. Yield: 5.14 g.

Infrared measurements were done on Thermo Nicole FT-IR spectrometer using KBr pellets and absorption bands are reported in reciprocal centimeter. $^1$H-NMR spectra and $^{13}$C-NMR spectra were recorded at 400 MHz NMR spectrometer. Mass spectra were recorded on Thermo Finnigan LCQ Advantage Max using ESI technique.

Certain modifications and improvements of the disclosed invention will occur to those skilled in the art without departing from the scope of invention, which is limited only by the appended claims.

We claim:

1. A process for producing 1-benzyl-4-[(5,6-dimethoxy-1-indanon-2-yl)methyl]piperidine of formula (1) or its salt thereof employing a novel intermediate, the process comprising:
   (a) oxidizing 4-[(5,6-dimethoxy-1-indanon-2-ylidene)methyl]pyridine of formula (4) using oxidizing agent in presence of solvent to get 4-[(5,6-dimethoxy-1-indanon-2-ylidene)methyl]pyridine N-oxide of formula (3) a novel intermediate,
   (b) reducing 4-[(5,6-dimethoxy-1-indanon-2-ylidene)methyl]pyridine N-oxide of formula (3) in presence of hydrogenating catalyst in solvent to yield 4-[(5,6-dimethoxy-1-indanon-2-yl)methyl]piperidine of formula (2) or its salt thereof,
   (c) treating 4-[(5,6-dimethoxy-1-indanon-2-yl)methyl]piperidine of formula (2) or its salt thereof with benzylating agent in presence of base and solvent, optionally in presence of phase transfer catalyst to produce 1-benzyl-4-[(5,6-dimethoxy-1-indanon-2-yl)methyl]piperidine of formula (1) or its salt thereof.

2. A process for producing 1-benzyl-4-[(5,6-dimethoxy-1-indanon-2-yl)methyl]piperidine of formula (1) or its salt thereof employing a novel intermediate, the process comprising:
   (a) reducing selectively the double bond of 4-[(5,6-dimethoxy-1-indanon-2-ylidene)methyl]pyridine of formula (4) in presence of catalyst in solvent to get 4-[(5,6-dimethoxy-1-indanon-2-yl)methyl]pyridine of formula (5),
   (b) treating 4-[(5,6-dimethoxy-1-indanon-2-yl)methyl]pyridine of formula (5) with an oxidizing agent in presence of solvent to get 4-[(5,6-dimethoxy-1-indanon-2-yl)methyl]pyridine N-oxide of formula (6) a novel intermediate,
   (d) reducing 4-[(5,6-dimethoxy-1-indanon-2-yl)methyl]pyridine N-oxide of formula (6) in presence of hydrogenating catalyst in solvent to yield 4-[(5,6-dimethoxy-1-indanon-2-yl)methyl]piperidine of formula (2) or its salt thereof,
   (e) treating 4-[(5,6-dimethoxy-1-indanon-2-yl)methyl]piperidine of formula (2) or salt thereof (2) with benzylating agent in presence of base and solvent, optionally in presence of phase transfer catalyst to produce 1-benzyl-4-[(5,6-dimethoxy-1-indanon-2-yl)methyl]piperidine of formula (1) or its salt thereof.

3. The process according to any of claim 1 or 2, wherein an oxidizing agent is selected from the group comprising peracids, oxiranes, peroxides, or metalloorganic agents.

4. The process according to claim 3, wherein an oxidizing agent is selected from the group comprising peracetic acid, caro's acid, m-chloroperoxybenzoic acid, oxaziridines, dimethyldioxirane (DMD), hydrogen peroxide-acetic acid, bis(trimethylsilyl)peroxide (BTSP), hydrogen peroxide-manganese tetrakis(2,6-dichlorophenyl)porphyrin, hydrogen peroxide-methyltrioxorhenium (MTO).

5. The process according to step a of claim 1 or step b of claim 2, wherein solvent used is selected from the group consisting of lower alcohols having 1 to 4 carbon atoms, chlorinated hydrocarbons such as methylene chloride, nitriles such as acetonitrile, amidic solvents such as dimethylformamide and water or mixture thereof.

6. The process according to any of claim 1 or 2, wherein hydrogenating catalyst is selected from noble metals or their derivatives.

7. The process of step b of claim 1 or step c of claim 2, wherein solvent used is selected from the group consisting of ethers such as dibutyl ether, methyl tert-butyl ether, dioxane and tetrahydrofuran, lower alcohols such as methanol, ethanol, propanol, isopropanol and butanol, chlorinated hydrocarbons such as methylene chloride, esters such as ethyl acetate and isopropyl acetate; polar aprotic solvents such as dimethylformamide, dimethylsulfoxide, N-methylpyrrolidone and water or mixture thereof.

8. The process according to any of claim 1 or 2, wherein the benzylating agent is selected from the group comprising benzyl chloride, benzyl bromide, benzyl iodide, benzyl mesylate or benzyl tosylate.

9. The process according to any of claim 1 or 2, wherein the base is an inorganic or organic base.

10. The process according to claim 9, wherein an inorganic base is selected from the group comprising carbonates or bicarbonates of alkali metal.

11. The process according to claim 10, wherein the alkali metal is selected from potassium, sodium or lithium.

12. The process according to claim 9, wherein an organic base is selected from the group comprising triethyl amine, pyridine, N-methyl morpholine, N,N-dimethyl benzyl amine, picoline or lutidine.

13. The process according to any of claim 1 or 2, wherein the phase transfer catalyst is selected from group comprising ammonium based phase transfer reagent, phosphonium based phase transfer reagent, crown ethers or polyethylene glycols.

14. The process according to claim 13, wherein phase transfer catalyst is selected from tetrabutylammonium iodide, tetrabutylammonium bromide, tetrabutylammonium hydrogen sulfate, benzyl triethylammonium chloride, benzyl tributylammonium chloride, tetramethylammonium chloride, tetrabutylphosphonium chloride, dibenzo-18-crown-6, PEG-200 or PEG-400.

15. The process according to step c of claim 1 or step d of claim 2, wherein solvent comprises one or more of ethers, alcohols, chlorinated hydrocarbons, esters, ketones, hydrocarbons, polar aprotic solvents and water or mixture thereof.

16. The process according to step a of claim 2, wherein the catalyst is selected from the group comprising Zn/CH3COOH, Fe/HCl or Raney Ni or noble metals for example platinum, palladium, rhodium, ruthenium or their derivatives in presence of catalytic amount of acid.

17. The process according to step a of claim 2, wherein solvent used is selected from the group consisting of ethers such as dibutyl ether, methyl tert-butyl ether, dioxane and tetrahydrofuran, lower alcohols such as methanol, ethanol, propanol, isopropanol and butanol, chlorinated hydrocarbons such as methylene chloride, esters such as ethyl acetate and isopropyl acetate, polar aprotic solvents such as dimethylformamide, dimethylsulfoxide, N-methylpyrrolidone and water or mixture thereof.

18. A novel intermediate 4-[(5,6-dimethoxy-1-indanon-2-ylidene)methyl]pyridine N-oxide of formula (3) for producing 1-benzyl-4-[(5,6-dimethoxy-1-indanon-2-yl)methyl]piperidine of formula (1) or its salt thereof.

19. A process for preparation of a novel intermediate 4-[(5,6-dimethoxy-1-indanon-2-ylidene)methyl]pyridine N-oxide of formula (3) for producing 1-benzyl-4-[(5,6-dimethoxy-1-indanon-2-yl)methyl]piperidine of formula (1) or its salt thereof; The process comprising oxidizing 4-[(5,6-dimethoxy-1-indanon-2-ylidene)methyl]pyridine of formula (4) using oxidizing agent in presence of solvent.

20. A novel intermediate 4-[(5,6-dimethoxy-1-indanon-2-yl)methyl]pyridine N-oxide of formula (6) for producing 1-benzyl-4-[(5,6-dimethoxy-1-indanon-2-yl)methyl]piperidine of formula (1) or its salt thereof.

21. A process for preparation of a novel intermediate 4-[(5,6-dimethoxy-1-indanon-2-yl)methyl]pyridine N-oxide of formula (6) for producing 1-benzyl-4-[(5,6-dimethoxy-1-indanon-2-yl)methyl]piperidine of formula (1) or its salt thereof; The process comprising oxidizing 4-[(5,6-dimethoxy-1-indanon-2-yl)methyl]pyridine of formula (5) using oxidizing agent in presence of solvent.

22. The process according to any of claim 19 or 21, wherein an oxidizing agent is selected from the group comprising peracetic acid, caro's acid, m-chloroperoxybenzoic acid, oxaziridines, dimethyldioxirane (DMD), hydrogen peroxide-acetic acid, bis(trimethylsilyl)peroxide (BTSP), hydrogen peroxide-manganese tetrakis(2,6-dichlorophenyl)porphyrin, hydrogen peroxide-methyltrioxorhenium (MTO).

23. The process according to any of claim 19 or 21, wherein solvent used is selected from the group consisting of lower alcohols having 1 to 4 carbon atoms, chlorinated hydrocarbons such as methylene chloride, nitriles such as acetonitrile, amidic solvents such as dimethylformamide and water or mixture thereof.

24. A process for preparing 4-[(5,6-dimethoxy-1-indanon-2-yl)methyl]piperidine of formula (2) or salt thereof for production of 1-benzyl-4-[(5,6-dimethoxy-1-indanon-2-yl)methyl]piperidine of formula (1) or its salt thereof, the process comprising:

(a) oxidizing 4-[(5,6-dimethoxy-1-indanon-2-ylidene)methyl]pyridine of formula (4) using oxidizing agent in presence of a solvent to get 4-[(5,6-dimethoxy-1-indanon-2-ylidene)methyl]pyridine N-oxide of formula (3), (b) reducing 4-[(5,6-dimethoxy-1-indanon-2-ylidene)methyl]pyridine N-oxide of formula (3) in presence of hydrogenating catalyst in solvent to yield 4-[(5,6-dimethoxy-1-indanon-2-yl)methyl]piperidine of formula (2) or its salt thereof.

25. A process for preparing 4-[(5,6-dimethoxy-1-indanon-2-yl)methyl]piperidine of formula (2) or salt thereof for production of 1-benzyl-4-[(5,6-dimethoxy-1-indanon-2-yl)methyl]piperidine of formula (1) or its salt thereof; The process comprising:

(a) reducing selectively the double bond of 4-[(5,6-dimethoxy-1-indanon-2-ylidene)methyl]pyridine of formula (4) in presence of a catalyst in solvent to get 4-[(5,6-dimethoxy-1-indanon-2-yl)methyl]pyridine of formula (5), (b) treating 4-[(5,6-dimethoxy-1-indanon-2-yl)methyl]pyridine of formula (5) with an oxidizing agent in presence of a solvent to get 4-[(5,6-dimethoxy-1-indanon-2-yl)methyl]pyridine N-oxide of formula (6) a novel intermediate, (c) reducing 4-[(5,6-dimethoxy-1-indanon-2-yl)methyl]pyridine N-oxide of formula (6) in presence of hydrogenating catalyst in solvent to yield 4-[(5,6-dimethoxy-1-indanon-2-yl)methyl]piperidine of formula (2) or its salt thereof.

26. A process for preparing 1-benzyl-4-[(5,6-dimethoxy-1-indanon-2-yl)methyl]piperidine of formula (1) or its salt thereof from compound 4-[(5,6-dimethoxy-1-indanon-2-ylidene)methyl]pyridine N-oxide of formula (3) or 4-[(5,6-dimethoxy-1-indanon-2-yl)methyl]pyridine N-oxide of formula (6) without isolating the intermediate 4-[(5,6-dimethoxy-1-indanon-2-yl)methyl]piperidine of formula (2) comprising:
  (a) reducing the compound 4-[(5,6-dimethoxy-1-indanon-2-ylidene)methyl]pyridine N-oxide of formula (3) or 4-[(5,6-dimethoxy-1-indanon-2-yl)methyl]pyridine N-oxide of formula (6) in presence of hydrogenating catalyst in solvent,
  (b) removing the hydrogenating catalyst from the reaction mixture,
  (c) reacting the reaction mixture obtained from step b with benzylating agent and base in solvent, optionally in the presence of phase transfer catalyst to produce 1-benzyl-4-[(5,6-dimethoxy-1-indanon-2-yl)methyl]piperidine of formula (1) or its salt thereof.

* * * * *